United States Patent [19]

Warren et al.

[11] Patent Number: 4,785,084

[45] Date of Patent: Nov. 15, 1988

[54] METHOD OF PREPARING PERACETYL OXAZOLINES

[75] Inventors: Christopher Warren, Carlisle, Mass.; Satoru Nakabayashi, Kawasakishi, Japan; Roger W. Jeanloz, Newton, Mass.

[73] Assignee: The General Hospital Corporation, Boston, Mass.

[21] Appl. No.: 891,282

[22] Filed: Jul. 31, 1986

[51] Int. Cl.[4] .................. C08B 37/00; C07H 15/00; C07H 17/00; C07H 17/02

[52] U.S. Cl. .................. 536/17.9; 536/17.4; 536/124

[58] Field of Search .............. 536/17.4, 17.9, 124

[56] References Cited

PUBLICATIONS

Srivastava, V. K., *Carbohydr. Res.*, 103:286-292, (1982).
Matta et al., *Carbohydr. Res.*, 21:460-464, (1972).
Warren, C. D. et al., *Carbohydr. Res.*, 92:85-101, (1980).
Warren, C. D. et al., *Carbohydr. Res.*, 61:181-196, (1978).
Warren, C. D. et al., *Carbohydr. Res.*, 126:61-80, (1984).
Ogawa, T. et al., *Carbohydr. Res.*, 136:135-152, (1985).
Auge, C. et al., *Carbohydr. Res.*, 82:85-95, (1980).
Reynolds, D. D. et al., *J. Amer. Chem. Soc.*, 62:66-69, (1940).
Warren, C. D. et al., *Carbohydr. Res.*, 82:71-83, (1980).

*Primary Examiner*—Ronald W. Griffin
*Attorney, Agent, or Firm*—Saidman, Sterne, Kessler & Goldstein

[57] ABSTRACT

This invention relates to a method of producing peracetyl oxazolines from peracetyl saccharides. The method involves reacting the starting material, a peracetyl saccharide, with a reactive compound, such as trifilic acid, to directly produce the peracetyl oxazoline.

7 Claims, No Drawings

METHOD OF PREPARING PERACETYL OXAZOLINES

FIELD OF THE INVENTION

This invention relates to a direct method of synthesizing peracetyl oxazolines from peracetyl saccharides.

BACKGROUND OF THE INVENTION

Glycoproteins are one of the major components of animal cell surfaces. The cell surfaces are usually coated with carbohydrate molecules which are attached to specific surface proteins to form glycoproteins. The glycoproteins are present in the outer protein layer of the cell's plasma membrane.

These cell surfaces contain specific recognition sites that interact with biological substances. For example, membrane surfaces contain certain areas capable of acting as antigens. Researchers are investigating how cells recognize other cells as "foreign" to understand how to treat tissue rejection and autoimmune diseases. N-linked glycan chains of glycoproteins (N-glycoproteins) are considered to be responsible for many of the cell site's biological recognition mechanisms. Thus, the understanding of the N-glycoprotein saccharide processing and function is of major interest. To study the N-glycoproteins, these compounds need to be first synthesized.

One of the steps in N-glycoprotein biosynthesis is the formation of "lipid intermediates." The oligosaccharide chains of the N-glycoproteins are assembled on a "lipid intermediate" prior to transfer of protein. Thus, oligosaccharide "lipid intermediates" are required as exogenous glycosyl acceptors for studies of N-glycoprotein biosynthesis. Herscovics, et al., *FEBS Lett.*, 156: 298-302 (1983); Sasak et al., *J. Biol. Chem.*, 259: 332-337 (1984).

Oligosaccharides with structures corresponding to those in the N-glycoprotein saccharide "core" may be isolated from the urine of animals with swainsonine-induced alpha-mannosidosis. Sadeh et al., *FEBS Lett.*, 163: 104-109 (1983); Daniel et al., *Biochem. J.*, 221: 601-607 (1984). These oligosaccharides may be isolated also by chemical [M. Fukuda et al. *J. Biochem* (Tokyo) 80: 1223-1232 (1976)] and enzymic [F. K. Chu, *J. Biol. Chem.*, 261: 172-177 (1986); A. L. Tarentino et al., *Biochemistry*, 24: 4665-4671 (1985)] degradation of glycoproteins, such as ovalbumin or ribonuclease B.

These oligosaccharides may also be synthesized for use as lipid intermediates. Synthesis of these oligosaccharides is accomplished by formation of a peracetylglycosyl phosphate, then coupling this compound with an "activated" derivative of dolichyl phosphate to produce a peracetyl diphosphate diester. This resulting compound is O-deacetylated to form the oligosaccharide "lipid intermediate." Warren et al., *Carbohydr. Res.*, 126: 61-80 (1984). Chemical synthesis is preferable over the isolation of natural compounds for obtaining suitable glycosyl acceptors since the synthesis ensures relatively large quantities of pure compounds having known structures.

The peracetylglycosyl phosphate, the first compound formed in the synthesis of the "lipid intermediate," is produced from peracetyl oxazolines. The peracetyl oxazolines are appropriate precursors of peracetylglycosyl phosphates because (a) these compounds provide the alpha anomer in a reaction that involves net retention of configuration and (b) phosphorylation occurs without any scission or modification of interresidue glycosidic linkages. Warren et al., *Carbohydr. Res.*, 126: 61-80 (1984); Warren et al., *Carbohydr. Res.*, 61: 181-196 (1978); and, Warren et al., *Carbohydr. Res.*, 92: 85-101 (1981).

A key step then in producing the oligosaccharide "lipid intermediates" is the preparation, in high yield, of a peracetyl oxazoline that can then be phosphorylated to produce the peracetylglycosyl phosphate, the synthetic precursor of an oligosaccharide "lipid intermediate." The synthesis of a lipid intermediate from a peracetyl oxazoline is as follows (Equation 1):

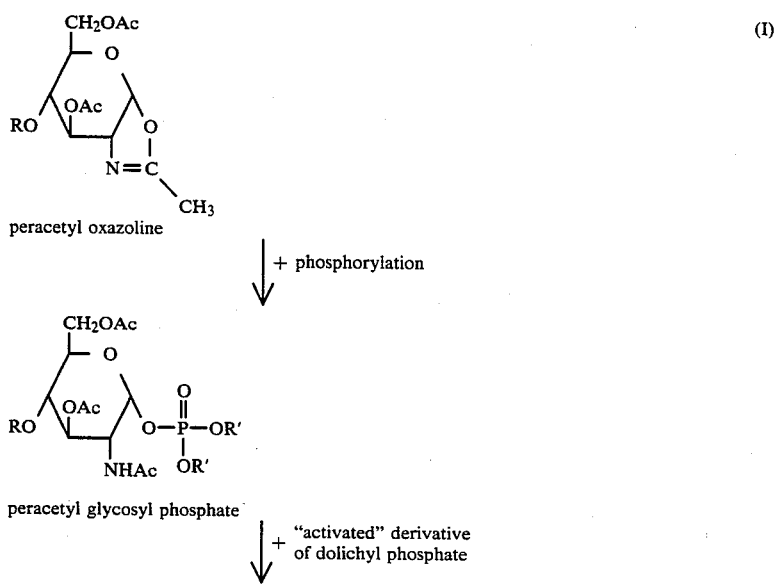

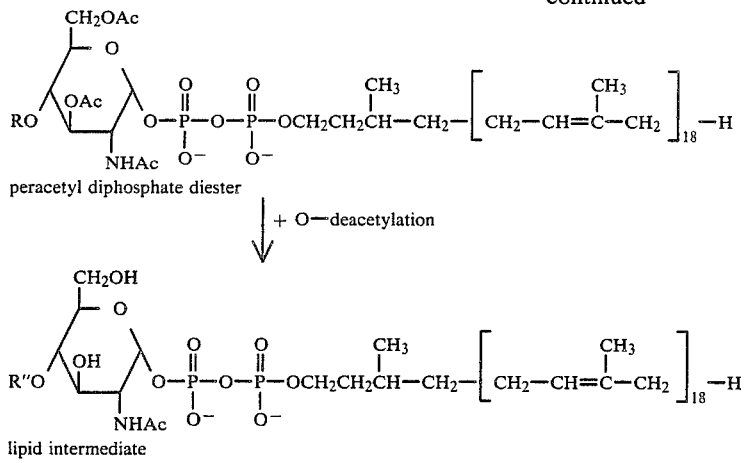
peracetyl diphosphate diester

↓ + O—deacetylation

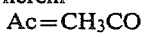
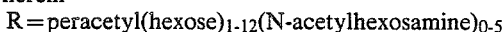
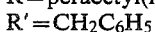
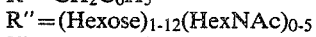
lipid intermediate wherein
Ac=CH₃CO
wherein
R=peracetyl(hexose)$_{1-12}$(N-acetylhexosamine)$_{0-5}$
R'=CH₂C₆H₅
R''=(Hexose)$_{1-12}$(HexNAc)$_{0-5}$ The peracetyl oxazolines are produced from peracetyl oligosaccharides. The synthesis of a peracetyl oxazoline from a peracetyl oligosaccharide is difficult due to the alpha (1→6) linkages in the oligosaccharide. These are very labile to the acidic conditions normally employed for formation of peracetyl oligosaccharide halides, the usual precursor of the peracetyl oxazoline. Also, because the oligosaccharides contain a di-N-acetylchitobiose residue, any reagents employed must not adversely affect the acetamido groups, or cause significant hydrolysis of the beta-(1→4) linkage between the two glycosylaminoacetyl (GlcNAc) residues. Thus chloroacetolysis, the treatment of saccharides with HCl in acetyl chloride, which was successfully employed for the preparation of glycosyl chlorides from oligosaccharides, cannot be used. (Warren et al. *Carbohydr. Res.*, 61, 92, and 126, supra.)

Alternative reagents for producing an oxazoline from a peracetyl saccharide are also problematic. For example, the use of ferric chloride as the reactive compound is of limited value since it only will react with the beta-D-anomer of a peracetyl saccharide, and the preferred starting material is the alpha peracetyl saccharide, because this is the anomer readily available by the action of pyridine-acetic anhydride on an oligosaccharide. (Matta et al., *Carbohydr. Res.*, 21: 460–464 (1972)). Further, stannic chloride, as the reactive compound with the alpha-D-anomer of peracetyl glucosamine, is efficient only when used with the monosaccharide. With oligosaccharides as the starting material, the reaction is incomplete, and side reactions produce low yields. (Srivastava, *Carbohydr. Res.*, 103: 286–292 (1982)).

Therefore, it would be desirable to develop a method of synthesis for obtaining peracetyl oxazolines from peracetyl saccharides.

SUMMARY OF THE INVENTION

This invention relates to a method of producing peracetyl oxazolines from peracetyl saccharides. The method involves reacting the starting material, a peracetyl saccharide, with a reactive compound, capable of generating the formation of an intermediate saccharide acetoxonium ion to directly produce the peracetyl oxazoline.

DETAILED DESCRIPTION OF THE INVENTION

In accordance with the invention, a peracetyl oxazoline can be prepared from a peracetyl saccharide by treatment with a reactive compound capable of generating the formation of an intermediate saccharide acetoxonium ion. Mono-, di-, and oligoperacetyl oxazolines can be prepared by the process of this invention.

The reaction for producing peracetyl oxazolines from peracetyl saccharides, and the use of the peracetyl oxazolines in the synthesis of lipid intermediates to then form N-glycoproteins is as follows (Equation 2):

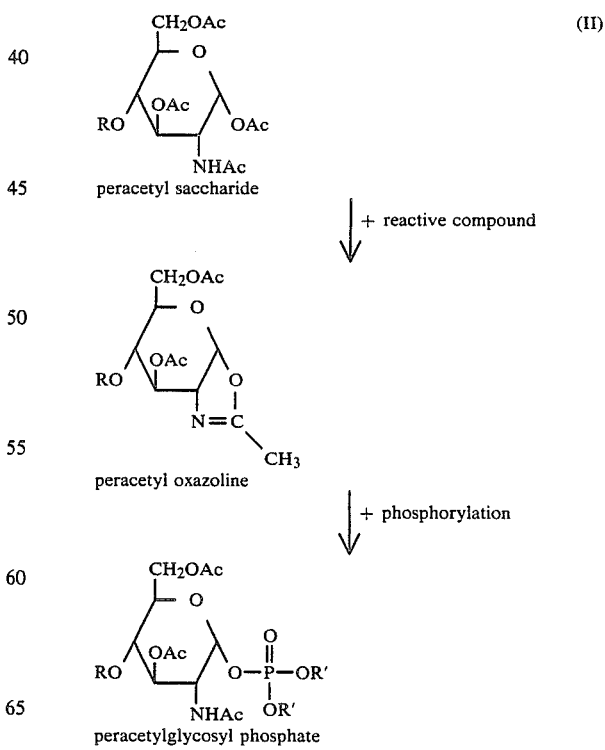

wherein Ac=CH₃CO wherein R=peracetyl(hexose)$_{1-12}$(N-acetylhexosamine)$_{0-5}$ Any naturally occurring or synthetic mono-, di-, or oligosaccharide that contains a hexosamine or N-acetylhexosamine at the reducing terminus of the saccharide may be used as the starting peracetyl saccharide in this invention. The peracetyl oligosaccharide that may be used in this invention, will typically be less than 14 residue units. The oligosaccharides will typically contain 1 to 12 residues of neutral hexoses, and either 1 or more residues of an N-acetylhexosamine. In addition, the peracetyl saccharide may be either the alpha or the beta anomer. (Warren et al. *Carbohydrate Res.*, 82: 71-83 (1980); Auge et al., *Carbohyrdrate Res.*, 82: 85-95 (1980); Warren et al., *Carbohydrate Res.*, 92: 85-101 (1981); Warren et al., *Carbohyrdate Res.*, 116: 171-182 (1983)).

The peracetyl saccharide is reacted with a reactive compound capable of generating the formation of an intermediate saccharide acetoxonium ion. Compounds capable of generating the formation of an intermediate saccharide acetoxonium ion to produce the desired peracetyl oxazoline include, but are not limited to, trifluoromethanesulfonic acid (triflic acid), and derivatives of trifluoromethanesulfonic acid, trimethylsilyl trifluoromethanesulfonate (TMS triflate), other triflates, such as triflates of silver and sodium, trifluoromethanesulfonic anhydride, and trifluoromethanesulfonyl chloride.

In the process according to this invention, the peracetyl saccharide reacts with the reactive compound, such as triflic acid, to directly produce the peracetyl oxazoline via the acetoxonium ion as follows (Equation 3):

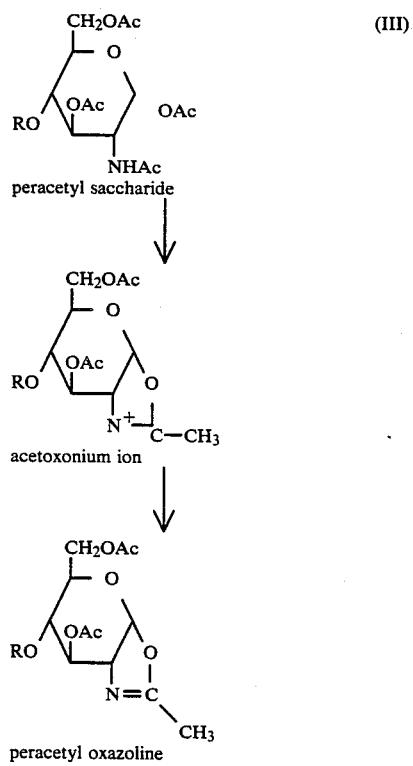

wherein Ac=CH$_3$CO wherein R=peracetyl(hexose)$_{1-12}$(N-acetylhexosamine)$_{0-5}$ The peracetyl saccharide is reacted with the reactive compound in an amount of from about 1:1 to about 1:2 moles per moles of starting material to reactive compound.

The reaction conditions include reaction temperature of from about 20° C. to about 50° C.; reaction time of from about 13 to about 40 hours. The reaction can be followed by thin-layer chromatography on glass plates coated with silica gel in 10:1 (v/v) chloroform-methanol.

After the reaction is completed, the produced peracetyl oxazoline can be recovered by means known in the art. In one embodiment, the reaction mixture is made slightly alkaline (pH 8) by addition of triethylamine, then the oxazoline is purified by column chromatography on Merck Kieselgel 60 (230-400 mesh) with elution by 100:200:1 toluene—ethyl acetate—acetonitrile—triethylamine. The yield is approximately 90% based on the peracetyl saccharide.

The peracetyl oxazolines produced according to the process of this invention have various uses. The peracetyl oxazolines can be used as glycosyl donors for oligosaccharide synthesis, for example as described in Warren et al., *Carbohydrate. Res.*, 92: 85-101 (1980). The oxazolines can be used specifically for synthesis of alpha-D-glycosyl phosphates, en route to biosynthetic lipid intermediates, for example as described in Warren et al., *Carbohydr. Res.*, 126: 61-80 (1984). The peracetyl oxazolines can be used in the synthesis of glycopeptides for the study of N-glycoprotein-saccharide processing and for the study for mammalian endobeta-N-acetyl-glucosaminidase.

The peracetyl oxazolines of this invention are also useful for preparing other oligosaccharide derivatives in addition to N-glycoproteins. Treatment of the peracetyl oxazoline with azides, thiols, and alcohols and other sugars, produce glycopeptides or aminoglycosides, thioglycosides, and O-glycosides, respectively. With this reaction, a B-glycosidic bond is formed at the reducing N-acetylglucosaminyl residue.

The peracetyl oxazolines of this invention can also be used in the synthesis of a glycopeptide. In this process, the peracetyl oxazoline is reacted with an azide to produce a glycosyl azide. The thus formed glycoside is then hydrogenated to produce a glycosylamine. The hydrogenation can be accomplished according to means known in the art, such as hydrogenation in acetic acid-water in the presence of palladium. The glycosylamine is then coupled to an amino acid or a peptide via any exposed carboxylic group in the amino acid or peptide as described in Garg and Jeanloz, *Carbohydr. Res.*, 23: 437-439 (1972).

The peracetyl oxazolines of this invention can further be used in a process for the synthesis of oligoglycosides by reacting a peracetyl oxazoline with a thiol in the presence of borontrifluoride (BF$_3$). The thiol compound can include alkyl, alkenyl, and aryl thiols and acetates and benzoates of thiols. The peracetyl oxazoline and thiol are reacted together in approximately equimolar equivalent proportions. The thiol compound is present in an amount of about 3-5 mole equivalents. Reaction temperature will depend upon the thiol compound and may be from 20° C. to 100° C. The reaction may be followed by thin layer chromatography as described in Ferrier and Furneaux, *Methods Carbohydr. Chem,* 8: 251–253 (1980).

Moreover, the oxazolines can be used in the synthesis of intermediates for the glycosylation of peptides, for instance, to provide synthetic antigens. Pinto et al., *Carbohydr. Res.,* 124: 313–318 (1983).

Further, the peracetyl oxazolines can be used for attachment to a solid support for affinity chromatography. Columns for affinity chromatography using the peracetyl oxazolines of this invention may be prepared by processes well known in the art, including the following processes: (1) the peracetyl oxazolines are reacted with the methyl ester of an omega-hydroxy fatty acid to produce a glycoside. The methyl ester groups of the glycoside are then saponified to expose a free acid group for coupling to the solid support.

Having now generally described this invention, the same will be better understood by reference to specific examples, which are included herein for purposes of illustration only, and are not intended to be limiting unless otherwise specified.

EXAMPLE 1

Hydrogen chloride, previously employed by many workers for the preparation of glycosyl chlorides, was tried, with either peracetyl α-Man-(1→6)-β-Man-(1→4)-β-GlcpNAc-(1→4)-GlcpNAc (Compound I) or peracetyl α-Man-(1→6)-[α-Man-(1→3)]-α-Man-(1→6)-[α-Man-(1→3)]-β-Man-(1→4)-β-GlcpNAc-(1→4)-GlcpNAc, (Compound II), both predominantly the alpha anomers, as the starting compounds. This method was unsatisfactory because of inter-residue bond cleavage. The results are shown in Table 1. A study was initiated, using 2-acetamido-1,3,4,6-tetra-O-acetyl-2-deoxy-α-D-glucopyranose (Compound III) as a model compound, to try to identify a more satisfactory procedure. As can be seen from the results in Table 1, none of the reagents tried produced a high yield of a glycosyl halide from the alpha anomer of the starting compound.

The formulas of compounds I, II, and III are shown below.

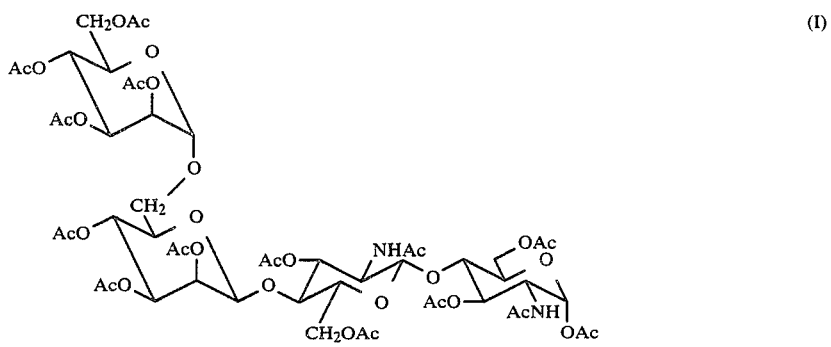

peracetyl α-Man-(1→6)-β-Man-(1→4)-β̄-GlcpNAc-(1→4)-GlcpNAc (I)

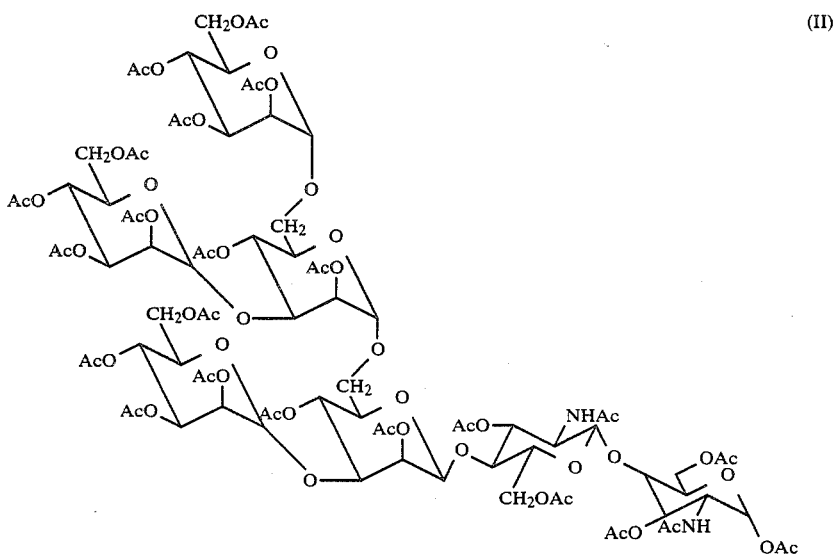

peracetyl α-Man-(1→6)-[α-Man-(1→3)]-α-Man-(1→6)-[α-Man-(1→3)]-β-Man-(1→4)-β-GlcpNAc-(1→4)-GlcpNAc (II)

2-acetamido-1,3,4,6-tetra-O-acetyl-2-deoxy-α-D glucopyranose (III)

TABLE 1

Formation of peracetylglycosyl halides from derivatives of 2-acetamido-2-deoxy-D-glucose.

| Starting compound | Reagent[a] | Result |
|---|---|---|
| I | HCl | ~40% yield of glycosyl chloride[b] |
| II | HCl | ~5-15% yield of glycosyl chloride[b] |
| III | TMS—Cl | No reaction |
| III | TMS—Br* | Low yield of glycosyl bromide, decomposition |
| III | TiCl$_4$** | Mixture of compounds[c], decomposition |
| III | TiBr$_4$*** | Mixture of compounds[c], decomposition |

*Gillard et al., Tetrahedron Lett., 22: 513-516 (1981).
**Nashed et al., Carbohydr. Res., 82: 237-252 (1980).
***Paulsen et al., Chem. Ber., 114: 3079-3101 (1981).
[a] All reactions were conducted at room temperature in 1,2-dichloroethane and the products identified by t.l.c.
[b] Evidence of major side reactions involving cleavage of glycosidic bonds.
[c] Compounds included glycosyl halide, oxazoline, and starting material.

EXAMPLE 2

Because of the problems described in Example 1, a new procedure was developed, involving reaction of a peracetyl oligosaccharide with trifluoromethanesulfonic acid (triflic acid). This reaction resulted in a direct formation of the oxazoline via the acetoxonium ion. Triflic acid was replaced by trimethylsilyl trifluoromethanesulfonate (TMS triflate), without any loss of yield (Table 2). Indeed, preliminary $^1$H-N.M.R. evidence indicated that triflic acid was the reactive species when the latter reagent was employed. This method was greatly superior to the use of stannic chloride (Srivastava, Carbohydr. Res., 103: 286-292 (1982)) which was found to be unsatisfactory for the efficient synthesis of oligosaccharide oxazolines.

When the TMS-triflate procedure was applied to Compound I, as shown in Example 1, $R_F$ 0.27 (20:1, v/v, chloroform—methanol), the tetrasaccharide oxazoline (R=peracetyl Man$_2$GlcNAc), $R_F$ 0.31 (same t.l.c. solvent) was obtained in 74% yield. The identity of the product was confirmed by the $^1$H-N.M.R. spectrum ($\delta$5.89 ppm, $J_{1,2}$7.3 Hz, H-1), and by hydrolysis at room temperature, with a dilute solution of p-toluenesulfonic acid in acetonitrile, followed by O-deacetylation with sodium methoxide in methanol, reduction with sodium borohydride, and comparison by high-pressure liquid chromatography (5 um Amino-Spherisorb column, acetonitrile—water 7:3) with an authentic specimen of the alditol derived from $\alpha$-Man-(1→6)-$\beta$-Man-(1→4)-$\beta$-GlcpNAc-(1→4)-GlcpNAc.

Similarly, when the TMS-triflate procedure was applied to Compound II, as shown in Example 1, $R_F$ 0.56 (10:1, v/v, chloroform—methanol), the heptasaccharide oxazoline (R=peracetyl Man$_5$GlcNAc), $R_F$ 0.60 (same t.l.c. solvent) was obtained in 90% yield. In neither case was there any t.l.c. evidence of formation of low molecular weight oxazolines indicative of glycosidic bond cleavage.

An important advantage of this new procuedure for the synthesis of oligosaccharide oxazolines is that it works equally well with the alpha or beta anomer of the starting peracetyl compound, unlike the ferric chloride method (Matta et al., Carbohydr. Res., 21: 460-464 (1972)) which can only utilize the relatively inaccessible beta anomer. The oxazoline derived from Compound I has been converted into a tetrasaccharide phosphate and employed for the synthesis of a "lipid intermediate." The oxazoline derived from compound II has been converted into a glycosyl azide and employed for the synthesis of a heptasaccharide-asparagine derivative.

TABLE 2

Formation of 2-methyl-(3,4,6-trio-O—acetyl-1,2-dideoxy-$\alpha$-D-glucopyrano)-[2,1-d]-2-oxazoline from 2-acetamido-1,3,4,6-tetra-O—acetyl-2-deoxy-$\alpha$-D-glucopyranose (Compound III)

| anomer of Compound III | reagent[a] | time (hours) | yield |
|---|---|---|---|
| alpha[b] | TMS-triflate | 16 | 95% |
| alpha[b] | Triflic acid | 12 | 97% |
| beta[c] | TMS-triflate | 0.5 | 100% |

[a] A solution of the starting compound (0.1 mmol) in 1,2-dichloroethane was stirred at 50° C. with 1.1 equiv. reagent. When t.l.c. (20:1, v/v chloroform-methanol) showed complete reaction, the reaction mixture was made slightly alkaline with excess triethylamine, applied to a column of silica gel (Merck Kieselgel 60; 230–400 mesh) and eluted with 1:2:0.01 toluene-ethyl acetate-triethylamine. The product had $R_F$ 0.43, $[\alpha]_D^{20}$ + 11° (C 1.35, chloroform) and was pure according to t.l.c. and H—N.M.R. spectrum.
[b] $R_F$ 0.37, $[\alpha]_D^{20}$ + 91° (C 1.4, chloroform).
[c] $R_F$ 0.34, $[\alpha]_D^{20}$ + 3° (C 1.75, chloroform).

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. A process for the production of a peracetyl oxazoline comprising reacting a peracetyl saccharide with a reactive compound selected from the group consisting of trifluoromethanesulfonic acid, trimethylsilyl trifluoromethanesulfonate, silver trifluoromethanesulfonate, sodium trifluoromethanesulfonate, trifluoromethanesulfonic anhydride, and trifluoromethanesulfonyl chloride, wherein said reactive compound is capable of generating the formation of an intermediate saccharide acetoxonium, ion to produce a peracetyl oxazoline.

2. The process according to claim 1 wherein said peracetyl saccharide is selected from mono-, di-, and oligosaccharides.

3. The process according to claim 1 wherein said reactive compound is trifluoromethanesulfonic acid.

4. The process according to claim 1 wherein said reactive compound is trimethylsilyl triflouromethanesulfonate.

5. A process for the synthesis of a peracetyl glycosyl phosphate comprising the steps of:

(a) reacting a peracetyl saccharide with a reactive compound selected from the group consisting of trifluoromethanesulfonic acid, trimethylsilyl trifluoromethanesulfonate, silver trifluoromethanesulfonate, sodium trifluoromethanesulfonate, trifluoromethanesulfonic anhydride, and trifluoromethanesulfonyl chloride, wherein said reactive compound is capable of generating the formation of an intermediate saccharide acetoxonium ion, to produce a peracetyl oxazoline, and (b) phosphorylating said peracetyl oxazoline to produce a peracetyl glycosyl phosphate.

6. A process for the synthesis of a glycopeptide comprising the steps of:

(a) reacting a peracetyl saccharide with a reactive compound selected from the group consisting of trifluoromethanesulfonic acid, trimethylsilyl trifluoromethanesulfonate, silver trifluoromethanesulfonate, sodium trifluoromethanesulfonate, trifluoromethanesulfonic anhydride, and trifluoromethanesulfonyl chloride, wherein said reactive compound is capable of generating the formation of an intermediate saccharide acetoxonium ion to produce a peracetyl oxazoline;

(b) reacting said peracetyl oxazoline with an azide to produce a glycosyl azide;

(c) hydrogenating said glycosyl azide to produce a glycosyl amine; and (d) coupling said glycosyl amine with an exposed carboxylic group in an amino acid or peptide.

7. A process for the synthesis of oligoglycosides comprising the steps of:

(a) reacting a peracetyl saccharide with a reactive compound selected from the group consisting of trifluoromethanesulfonic acid, trimethylsilyl trifluoromethanesulfonate, silver trifluoromethanesulfonate, sodium trifluoromethanesulfonate, trifluoromethanesulfonic anhydride, and trifluoromethanesulfonyl chloride, wherein said reactive compound is capable of generating the formation of an intermediate saccharide acetoxonium ion to produce a peracetyl oxazoline, and, (b) reacting said peracetyl oxazoline with a thiol compound in the presence of boron trifluoride.

* * * * *